United States Patent
Cosman

[19]
[11] Patent Number: 6,167,295
[45] Date of Patent: *Dec. 26, 2000

[54] OPTICAL AND COMPUTER GRAPHIC STEREOTACTIC LOCALIZER

[75] Inventor: Eric R. Cosman, Belmont, Mass.

[73] Assignee: Radionics, Inc., Burlington, Mass.

[*] Notice: This patent is subject to a terminal disclaimer.

[21] Appl. No.: 08/590,044

[22] Filed: Jan. 3, 1996

Related U.S. Application Data

[63] Continuation of application No. 08/205,138, Mar. 2, 1994, abandoned, which is a continuation of application No. 07/647,305, Jan. 28, 1991, abandoned.

[51] Int. Cl.$^7$ .................................................. A61B 5/00
[52] U.S. Cl. ...................... 600/426; 606/130; 600/414
[58] Field of Search .................. 128/653.1, 664, 128/665, 897, 920; 364/413.01, 413.13, 413.22; 606/130; 600/407, 410, 473, 476, 426, 414; 378/4, 205, 206

[56] References Cited

U.S. PATENT DOCUMENTS

| | | |
|---|---|---|
| 3,777,124 | 12/1973 | Pavkovich . |
| 3,821,469 | 6/1974 | Whetstone et al. . |
| 3,983,474 | 9/1976 | Kuipers . |
| 4,058,114 | 11/1977 | Soldner . |
| 4,068,156 | 1/1978 | Johnson et al. . |
| 4,182,312 | 1/1980 | Mushabac . |
| 4,262,306 | 4/1981 | Renner . |

(List continued on next page.)

FOREIGN PATENT DOCUMENTS

| | | |
|---|---|---|
| 0 018 166 | 10/1980 | European Pat. Off. . |
| 0 062 941 | 10/1982 | European Pat. Off. . |
| 0146699 | 7/1985 | European Pat. Off. . |
| 0 326 768 | 8/1989 | European Pat. Off. . |
| 0 359 773 | 3/1990 | European Pat. Off. . |
| 1282623 | 12/1961 | France . |

(List continued on next page.)

OTHER PUBLICATIONS

Adams, Ludwig et al., "Computer–Assisted Surgery", *IEEE Computer Graphics & Applications*, pp. 43–51, May 1990 (article).

Brown, Russell A., "A Stereotactic Head Frame for Use with CT Body Scanners", nvestigative Radiology, vol. 14, No.4, Jul.–Aug. 1979.

Castleman, Kenneth R., "Stereometric Ranging", *Digital Image Processing*, Prentice–Hall, Inc., Englewood Cliffs, New Jersey, 1979, pp.364–369 (Chapter from a Book).

(List continued on next page.)

*Primary Examiner*—Marvin M. Lateef
*Assistant Examiner*—Shawna J. Shaw

[57] ABSTRACT

This patent relates to an apparatus involving optical cameras, one or more, and computer graphic means for registering anatomical subjects seen in the cameras to computer graphic image displays of image data taken from CT, MRI or other scanning image means. One or more cameras may be set up to view the anatomical subject. The anatomical subject has been scanned previously by an imaging machine such as a CT scanner and the data has been stored in a computer with computergraphic readout. The computer has software which enables rotation translation and scaling of the anatomical subject seen in the image data. By registering the field of view of the camera or cameras with the corresponding graphic view of the image data, a registration of the optical view with the scanner image view can be made. In this way, points identifiable in the camera view can be located in the image data view and vice versa. In addition, if two views of the anatomical subject are taken, unique 3-dimensional coordinates of corresponding points between the camera to the image reconstructions can be determined. For instance, a space probe or microscope or surgical instrument can be quantitatively referenced to the anatomy with the scene of the camera field-of-view by reference to the identical scanner view. Thus, the position of the probe or its directional view toward the subject relative to internal anatomical structures can be determined. Index marks on the subject as seen in the camera and image may also be an adjunct to this technique.

7 Claims, 4 Drawing Sheets

U.S. PATENT DOCUMENTS

| | | |
|---|---|---|
| 4,319,136 | 3/1982 | Jinkins . |
| 4,341,220 | 7/1982 | Perry . |
| 4,358,856 | 11/1982 | Stivender et al. . |
| 4,386,602 | 6/1983 | Sheldon et al. . |
| 4,463,758 | 8/1984 | Patil et al. . |
| 4,465,069 | 8/1984 | Barbier et al. . |
| 4,473,074 | 9/1984 | Vassiliadis . |
| 4,506,676 | 3/1985 | Duska . |
| 4,583,538 | 4/1986 | Onik et al. ............................ 128/653.1 |
| 4,592,352 | 6/1986 | Patil . |
| 4,598,368 | 7/1986 | Umemura .......................... 364/413.22 |
| 4,602,622 | 7/1986 | Bar et al. . |
| 4,608,977 | 9/1986 | Brown . |
| 4,617,925 | 10/1986 | Laitinen . |
| 4,618,978 | 10/1986 | Cosman . |
| 4,638,798 | 1/1987 | Shelden et al. . |
| 4,651,732 | 3/1987 | Frederick . |
| 4,653,509 | 3/1987 | Oloff et al. . |
| 4,659,971 | 4/1987 | Suzuki et al. . |
| 4,660,970 | 4/1987 | Ferrano . |
| 4,674,057 | 6/1987 | Caughman et al. . |
| 4,686,997 | 8/1987 | Oloff et al. . |
| 4,698,777 | 10/1997 | Toyoda et al. . |
| 4,701,049 | 10/1987 | Beckman et al. . |
| 4,705,395 | 11/1987 | Hageniers . |
| 4,705,401 | 11/1987 | Addleman et al. . |
| 4,706,665 | 11/1987 | Gouda . |
| 4,709,756 | 11/1987 | Murphy et al. . |
| 4,722,056 | 1/1988 | Roberts et al. .................... 364/413.22 |
| 4,722,336 | 2/1988 | Kim at al. . |
| 4,723,544 | 2/1988 | Moore et al. . |
| 4,733,661 | 3/1988 | Palestrant . |
| 4,733,969 | 3/1988 | Case et al. . |
| 4,737,032 | 4/1988 | Addleman et al. . |
| 4,742,815 | 5/1988 | Ninan et al. . |
| 4,743,770 | 5/1988 | Lee . |
| 4,743,771 | 5/1988 | Sacks et al. . |
| 4,745,290 | 5/1988 | Frankel et al. . |
| 4,750,487 | 6/1988 | Zanetti . |
| 4,753,528 | 6/1988 | Hines et al. . |
| 4,760,851 | 8/1988 | Fraser et al. . |
| 4,761,072 | 8/1988 | Pryor . |
| 4,762,016 | 8/1988 | Stoughton et al. . |
| 4,764,016 | 8/1988 | Johansson . |
| 4,776,749 | 10/1988 | Wanzenberg et al. . |
| 4,779,212 | 10/1988 | Levy . |
| 4,782,239 | 11/1988 | Hirose et al. . |
| 4,791,934 | 12/1988 | Brunnett . |
| 4,794,262 | 12/1988 | Sato et al. . |
| 4,797,736 | 1/1989 | Kloots et al. . |
| 4,805,615 | 2/1989 | Carol . |
| 4,809,694 | 3/1989 | Ferrara . |
| 4,821,200 | 4/1989 | Oberg . |
| 4,821,206 | 4/1989 | Arora . |
| 4,822,163 | 4/1989 | Schmidt . |
| 4,825,091 | 4/1989 | Breyer et al. . |
| 4,826,487 | 5/1989 | Winter . |
| 4,829,373 | 5/1989 | Leberl et al. . |
| 4,835,710 | 5/1989 | Schnelle et al. . |
| 4,836,778 | 6/1989 | Baumrind et al. . |
| 4,838,265 | 6/1989 | Cosman et al. . |
| 4,841,967 | 6/1989 | Chang et al. . |
| 4,845,626 | 7/1989 | Ohhashi . |
| 4,859,181 | 8/1989 | Neumeyer . |
| 4,869,247 | 9/1989 | Howard, III et al. . |
| 4,875,478 | 10/1989 | Chen . |
| 4,884,566 | 12/1989 | Mountz et al. . |
| 4,896,673 | 1/1990 | Rose et al. . |
| 4,931,056 | 6/1990 | Ghajar et al. . |
| 4,933,843 | 6/1990 | Scheller et al. . |
| 4,943,296 | 7/1990 | Funakubo et al. . |
| 4,945,914 | 8/1990 | Allen . |
| 4,955,891 | 9/1990 | Carol . |
| 4,961,422 | 10/1990 | Marchosky et al. . |
| 4,979,222 | 12/1990 | Weber . |
| 4,985,019 | 1/1991 | Michelson . |
| 4,991,579 | 2/1991 | Allen . |
| 5,016,639 | 5/1991 | Allen .................................. 364/413.13 |
| 5,017,139 | 5/1991 | Mushabac . |
| 5,027,818 | 7/1991 | Bova et al. . |
| 5,047,036 | 9/1991 | Koutrouvelis . |
| 5,050,608 | 9/1991 | Watanabe et al. . |
| 5,052,035 | 9/1991 | Krupnick . |
| 5,056,523 | 10/1991 | Hotchkiss, Jr. et al. . |
| 5,070,454 | 12/1991 | Griffith .............................. 364/413.13 |
| 5,078,140 | 1/1992 | Kwon . |
| 5,080,662 | 1/1992 | Paul . |
| 5,086,401 | 2/1992 | Glassman et al. . |
| 5,094,241 | 3/1992 | Allen .................................. 364/413.13 |
| 5,097,839 | 3/1992 | Allen ...................................... 606/130 |
| 5,099,846 | 3/1992 | Hardy .................................. 364/413.13 |
| 5,107,839 | 4/1992 | Houdek et al. . |
| 5,116,344 | 5/1992 | Sundqvist . |
| 5,119,817 | 6/1992 | Allen .................................. 364/413.13 |
| 5,142,559 | 8/1992 | Wielopolski et al. . |
| 5,142,930 | 9/1992 | Allen et al. . |
| 5,147,372 | 9/1992 | Nymark et al. . |
| 5,154,179 | 10/1992 | Ratner . |
| 5,163,430 | 11/1992 | Carol . |
| 5,165,410 | 11/1992 | Warne et al. . |
| 5,173,946 | 12/1992 | Rao . |
| 5,178,146 | 1/1993 | Giese . |
| 5,186,174 | 2/1993 | Schlondorff et al. . |
| 5,193,106 | 3/1993 | DeSena . |
| 5,197,476 | 3/1993 | Nowacki et al. . |
| 5,198,977 | 3/1993 | Salb . |
| 5,207,223 | 5/1993 | Adler . |
| 5,211,164 | 5/1993 | Allen . |
| 5,224,049 | 6/1993 | Mushabac . |
| 5,230,338 | 7/1993 | Allen et al. . |
| 5,247,555 | 9/1993 | Moore et al. . |
| 5,251,127 | 10/1993 | Raab . |
| 5,257,998 | 11/1993 | Ota et al. . |
| 5,269,305 | 12/1993 | Corol . |
| 5,280,427 | 1/1994 | Magnusson et al. . |
| 5,285,787 | 2/1994 | Machida . |
| 5,295,483 | 3/1994 | Nowacki et al. . |
| 5,305,203 | 4/1994 | Raab . |
| 5,354,314 | 10/1994 | Hardy et al. . |
| 5,383,454 | 1/1995 | Bucholz . |
| 5,397,329 | 3/1995 | Allen . |
| 5,398,684 | 3/1995 | Hardy . |
| 5,622,170 | 4/1997 | Schulz . |
| 5,662,111 | 9/1997 | Cosman . |
| 5,792,146 | 8/1998 | Cosman . |
| 5,836,954 | 11/1998 | Heibrun et al. . |
| 5,848,967 | 12/1998 | Cosman . |

FOREIGN PATENT DOCUMENTS

| | | |
|---|---|---|
| 2417-970 | 10/1979 | France . |
| 2809645 | 11/1978 | Germany . |
| 3508730 | 9/1986 | Germany . |
| 62-327 | 6/1987 | Japan . |
| 0766581 | 9/1980 | Russian Federation . |
| 0955916 | 9/1982 | Russian Federation . |
| 1666093 | 7/1991 | Russian Federation . |
| 2 094 590 | 9/1982 | United Kingdom . |
| 2213066 | 8/1989 | United Kingdom . |
| WO88/09151 | 12/1988 | WIPO . |
| WO 90/05494 | 5/1990 | WIPO . |
| WO 91/07726 | 5/1991 | WIPO . |

OTHER PUBLICATIONS

Cinquin, P. et al., "Computer Assisted Medical Interventions", International Advanced Robotics Programme, The 2nd Workshop on Medical and Healthcare Robotics, Sep. 5–7, 1989.

"3–D Digitizer Captures the World", *Byte*, p. 43, Oct. 1990.

Foley, James D. et al., "Geometrical Transformations", *Fundamentals of Interactive Computer Graphics*, Second Edition, Addison–Wesley Publishing Company, 1984, Chapter 7, pp. 245–266 (Chapter from a Book).

Friets, Eric M. et al. "A Frameless Stereotaxic Operating Microscope for Neurosurgery", *IEEE Transactions of Biomedical Engineering*, vol. 36, No. 6, June 1989.

Fuchs, Henry et al., "Acquisition and Modeling of Human Body Form Data,"SPIE, vol. 166, Applications of Human Biosteriometrics (NATO) (1978).

Gonzales, Rafael C. et al., "Stereo Imaging", *Digital Image Processing*, Second Edition, Addison–Wesley Publishing Company, Section 2.2.2, pp. 52–54 (Section from a Book).

Jacques, Skip et al., "A Computerized Microstereotactic Method to Approach, 3–Dimensionally Reconstruct, Remoe and Adjuvantly Treat Small CNS Lesions", *Appl. Neurophysio.* 43:176–182 (1980).

Jiang, Hongjian et al., "A New Approach to 3–D Registration of Multimodality Medical Images by Surface Matching", Proceedings of SPIE *The Inter. Society for Optical Engineering*. Vol.1808:196–213 (1992).

Kato, Amami et al., "A frameless, armless navigational system for computer–assisted neurosurgery", *J. Neurosurg.*, No. 74, pp. 845–849, 1991.

Kosugi, Yukio et al., "An Articulated Neurosurgical Navigation System Using MRI and CT Images", *IEEE Transactions on Biomedical Engineering*, vol. 35, No.2, pp.147–152 Feb. 1988 (article).

Lavallee. S., "A New System for Computer Assisted Neurosurgery", *IEEE Advanced Topics in Biorobotics, Engineering in Medicine and Biology Society 11th Annual International Conference*(1989).

Lavallee, S. et al., "Computer Assisted Interventionist Imaging: The Instance of Stereotactic Brain Surgery", *Medinfo 89*, Part 1.

Lavallee, Stephane and Cinquin, Philippe, "Computer Assisted Medical Interventions", *3D Imaging in Medicine*, NATO ASI Series, vol. F 60 (1990).

Lavallee, S. et al., "Computer Assisted Puncture", Reconnaissance Des Formes et Intelligence Artificielle, 6th Congres Exposition, vol. 1, 439–49, Nov. 16–20, 1987.

Lemke, H.U. et al. (ed.), "Computer Assisted Radiology", Proceedings of the International Symposium CAR '89.

Mazier, B. et al., "Computer Assisted Interventionist Imaging: Application to the Vertebral Column Surgery", *Annual International Conference of the IEEE Engineering in Mewdicine and Biology Society*, vol. 12, No. 1 (1990).

Mazier, B. et al., "Computer Assisted Vertebral Column Surgery: Application to the Spinal Pedicle Fixation", *Innov. Techo. Biol. Med.*, vol. 11, No.5 (1990).

Mesqui, F. et al., "Real–Time, Noninvasive Recording and Three–Dimensional Display of the Functional Movements of an Arbitrary Mandible Point", SPIE vol. 602 Biostereometrics 85 (1986).

Murphy, Martin J., "An Automatic Six–Degree–of–Freedom Image Registration Algorithm for Image–Guided Frameless Stereotaxic Radiosurgery", Medical Physics, vol. 24, No. 6 (Jun. 1997) [added 7/28/99].

Newman and Sproull, "Moving Parts Of An Image", *Principles of Interactive Computer Graphics*, McGraw–Hill Book Company, 1979, Section 17.3, p. 254 (Section from a Book).

Pelizzari, C.A. et al., "Interactive 3D Patient –Image Registration", (date unknown).

Pixsys brochure on "3–D Digitizing Accessories", 4 pages (date unknown).

Pixsys manual for "Alignment Procedure for the Pixsys Two–Emitter Offset Probe for the SAC GP–8–3d Sonic Digitizer", 3 pages, Pixsys, 1319 Spruce Street, Suite 201, Bo9ulder, CO 80302 (no date).

Pixsys brochure, "Offset Probe for Science Accessories'Gp–8–3d digitizer "(Dec. 1987) by PixSys, Inc., one page.

Pixsys brochure "Design Aide"(Mar. 1989) by PixSys, Inc. 5 pages.

Reinhardt, H. et al., "A Computer–Assisted Device for the Intraoperative CT–Correlated Localization of Brain Tumors",*Eur. Surg. Res.*, pp.51–58, No. 20, 1988.

Reinhardt, H.F. and Landolt, H., "CT–Guided "Real–Time"Stereodaxy", *Acta Neuroschirurgica*, Suppl. 46, 107–108 (1989).

Reinhardt, H.F., "Interactive Sonar–Operanted Deviced for Stereotactic and Open Surgery", *Proceedings, of the Xth Meeting of the World Society for Stereotactic and Functional Neurosurgery, Maebashi, Japan, Oct. 1989*(1990).

Reinhardt, HJ., "Surgery of Brain Neoplasms Using 32–P Tumour Marker", *Acta Neurochirugica*, 97:89–94 (1989).

Roberts, David W. et al., "A Frameless Stereotaxic Integration of Computerized Tomography Imaging and The Operating Microscope", *J. Neurosurg.*65:545–549 (1986).

"SACDAC User's Guide", Version 2e Mar.2, 1989, 3–D coordinate acquisition software for the SAC GP8–3D digitizer and the IBM Personal Computer, PixSys, 1319 Spruce Street, Su8ite 201, Boulder, CO 80302.

Science Accessories Croporation brochure on Model GP–8–3D 3–Dimentional Sonic Digitizer (date unknown).

Watanabe, Eiju et al., "Three–Dimentional Digitizer (Neuronavigator): New Eguipment for Computed Tomography–Guided Stereotaxic Surgery", *Surg. Neurol.*, pp. 543–547, No. 27, 1987.

Watanabe, Hideyasu, "Neuronavigator", *Igaku–no–Ayumi*-(Medical Progress), vol. 137, No. 6 (May 10, 1986).

Wolfe, William L. et al., "Image Trackers", *The Infrared Handbook*, Environmentalk Research Institute of Michigan for the Office of Naval Research, 1978, pp. 22–63 — 22–77 (Chapter from a Book).

Wolff, Robert S. et al., "Through Canyons and Planets", *Visualization of Natural Phenomena*, First Edition, TELOS The Electronic Library of Science, Santa Clara, California, Chapter 3, pp. 66–67 (Chapter from a Book).

OPTICAL AND COMPUTER GRAPHIC STEREOTACTIC LOCALIZER

CROSS-REFERENCE TO RELATED APPLICATIONS

This application is a continuation of application Ser. No. 08/205,138, filed Mar. 2, 1994, and entitled "Optical and Computer Graphic Stereotactic Localizer," now abandoned, which is a continuation of application Ser. No. 07/647,305, filed Jan. 28, 1991, and entitled "Optical and Computer Graphic Stereotactic Localizer," now abandoned.

BACKGROUND TO THE INVENTION

The concept of frameless stereotaxy is now emerging in the field of neurosurgery. What is meant by this is quantitative determination of anatomical positions on, let us say, the head based on data taken from a CT, MRI or other scanning needs. The data from the image scan can be put into a computer and the head represented, according to this graphic information. It is useful for the surgeon to know where he will be operating relative to this data field. He can, thus, plan his operation quantitatively based on the anatomy as visualized from the image data. Until now the use of stereotactic head frames for fixation means is commonplace. These employ a head fixation device typically with an index means that can be visualized in scan slides or image data. Thus, the anatomical stereotactic data so determined can be quantified relative to the head frame. Arc systems or probe carriers are typically used to direct a probe quantitatively based on this data relative to the head holder and, thus, to the anatomy. If the surgeon can be freed from the use of the head holder and localizer, and still relate positions in the anatomy to things seen on the scan or image data, then this can spare patient discomfort and could be potentially used for general neurosurgery where only approximate target positioning is needed. For example, a space pointer which could be directed to the anatomy and its position could be quantified relative to the stereotactic image data. This space pointer, analogous to a pencil, might be therefore pointed at a position on the anatomy and the position and the direction of the pointer, subsequently appear, on the computer graphics display of the anatomical data. It would be convenient if this space pointer were mechanically decoupled or minimally mechanically coupled. Until now, several attempts have been made to implement a passive or active robotic pointer which consists of a pencil attached to an articulating arm, the arm having encoded joints which provide digital angular data. Such a robotic space pointer is a mechanically attached device and once calibrated can give the graphic representation of the pointer on a computer screen relative to the stereotactic data of the head.

One objective of the present invention is camera apparatus which can visualize a surgical field and digitize the view information from the camera and relate it via computer graphics means to image data which has been taken of the patient's anatomy by image scanning means. The relationship of the optical camera view and the image data will then make quantitative the anatomy seen in the camera view and also make quantitative the position of surgical instruments such as probes, microscopes, or space pointers to the anatomy via the registration of the camera view to the image data.

Another objective of the present invention is to make an optically coupled space pointer which accomplishes the same objectives as the robotic arm mechanically coupled space pointer. The optical coupling would free the surgeon from any sterility questions, provide a obstruction-free device, and avoid the encumbrances of a bulky mechanically coupled instrument.

DESCRIPTION OF THE INVENTION

Figure 1:
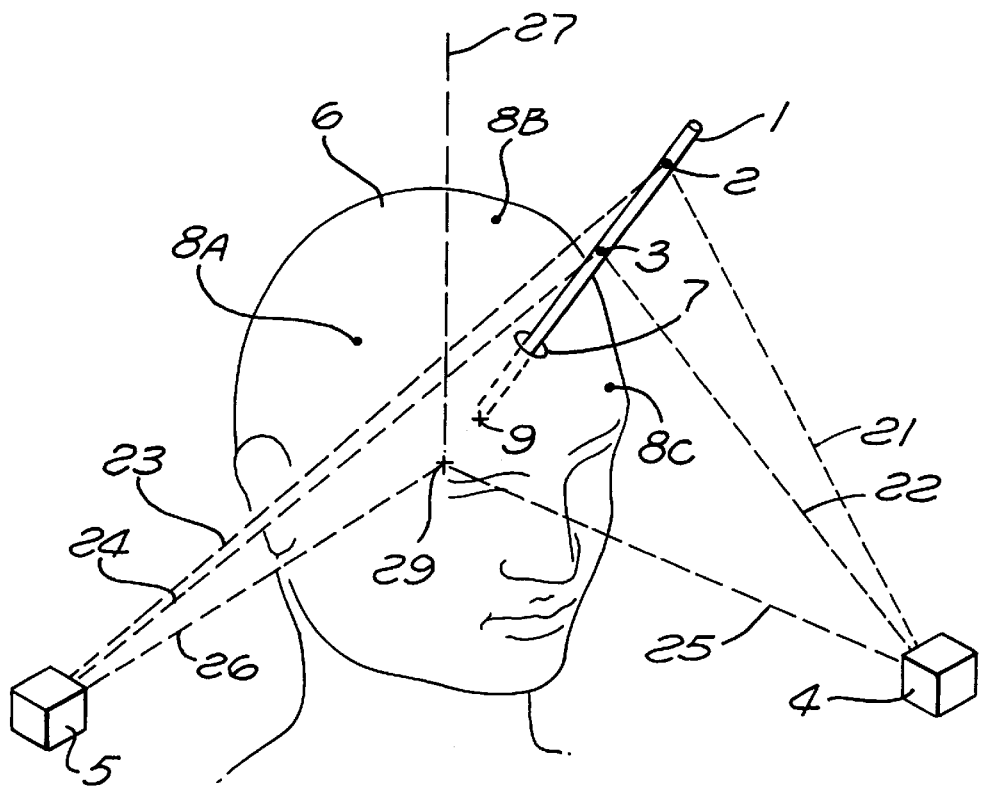
FIG. 1 shows one embodiment of the present invention which involves two video cameras and a space pointer with two light sources on it.

FIG. 1 shows a schematic view of one embodiment of the invention. The setting is neurosurgery and the patient 6 is being operated on through a skull hole 7. Probe 1 is being put up to the patient's head and it is desired to know the relationship of that probe to the anatomy of the patient's as visualized from some imaging means such as CT or MR scanners or angiographic X-rays views. This image data representation of the patient's head would previously have been accumulated in a computer. The cameras 4 and 5 may, for example be CCD Type compact TV Scanners with high resolution that can be easily digitized and video displayed or displayed on computer graphic screens. They are looking at the field including the patient's head 6 and the probe 1. The orientation and quantification of the data taken from the scan images in the video camera can be registered by can be registered by index spots 8A, 8B and 8C which may be placed on the patient's head. An alternative to these index spots might be a head ring which is fixed firmly to the patient's skull as is commonly done in surgery and that heading may have index points or lines on it which can be seen in the two views from the cameras 4 and 5. When the index points are in view of the cameras, the appropriate transformations can be made if the coordinates of the the physical points 8A, 8B, and 8C are known beforehand to the entire data set of anatomy in the computer. More than three points may also be used for redundancy or better field of view. The probe in FIG. 1 has two index light sources 2 and 3, which are also visible within a certain range to the cameras 4 and 5. Thus, the orientation of the light sources 2 and 3 relative to the anatomy is registered by the two cameras 4 and 5 and thus physical orientation of probe 1 relative to the head 6 is known. Since light sources 2 and 3 may be in a predetermined orientation relative to the tip of the probe 9, the actual physical location of the tip 9 relative to the anatomy may also be computed by the two views of the cameras 4 and 5. The orientation of the probe 1 may also be known from these two views. Thus, it is possible to display by the data accumulated by the cameras the orientation and absolute position of the probe relative to the anatomy, and this display can be made on computer graphics real time as the probe is moved around in a field near the anatomy. In particular, the probe within the entry hole 7 is known, and thus the tip 9 can be graphically visualized on a computer display relative to anatomy inside the patient's head. This is most useful when exploring the interior of a surgical hole when the surgeon wishes to know the advancement of his probe or surgical instruments within that hole. Such an instrument may also be useful in planning the position of a surgical incision. By pointing the probe at the patient's skin and being able to visualize the position on the skin relative to relevant anatomy inside the head, the surgeon can make a judicious choice of entry point.

The light sources 2 and 3 may be LED light sources of very small dimension and they can be powered by an internal battery in the probe 1. The probe may thus be mechanically decoupled from other apparatus and only optically coupled through the cameras 4 and 5. This optical coupling can be done in other ways. For example, there may be external light sources positioned nearby which can be reflected by tiny reflectors 2 and 3 on the probe. The reflected light can then be detected by cameras 4 and 5 giving the same optical registration of the probe position as though the light sources were sources of light on the probe itself.

Figure 2:
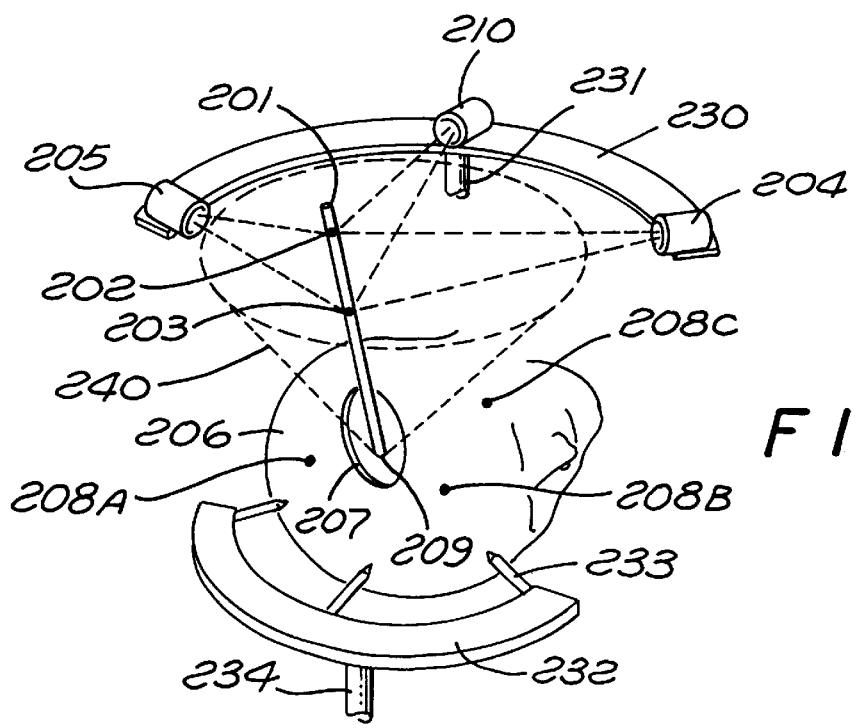
FIG. 2 shows an embodiment of the present invention with the space pointer pointing into a cranial operative site and where more than two video cameras are looking at the space pointer for redundancy.

Recalibration of the entire optical system is also possible. Cameras 4 and 5 may have principle optical axes, 25 and 26 respectively shown in FIG. 1. The cameras can be aligned to be pointing in a plane and directed towards a common isocenter 29. Thus all rays in the field such as rays 21 and 22 as seen from camera 4 to points 2 and 3 or rays 23 and 24 which also connect points 2 and 3 on the probe to the camera position 5 can be calibrated in the field of the cameras so that their exact angles relative to the principle rays indicated by 25 and 26 can be quantitatively determined. Once the quantitative orientation of these rays to the fiducial points 2 and 3 are digitized and determined numerically, then the position and orientation of the probe 1 can be calculated relative to the point 29 which has been recalibrated. The exact referencing of the coordinate system represented by axes 25 and 26 with their crossover point 29 and orthogonal axis 27 can be determined by further fiducial points on the anatomy itself. Natural anatomical fiducial points can be used such as the tip of the nose, the ears or other bony landmarks. However, specific index points such as 8A, 8B, and 8C can be placed on the patient's scalp, for example, and these used as a reference transformation set to relate the data seen by the cameras to anatomical data determined from the imaging. For example, the exact coordinates of the points 8A, 8B, and 8C may have been determined in space from the scan data previously. By knowing their exact coordinates in space and knowing the position of other anatomy relative to them, by determining the position as seen by the cameras 4 and 5 of these three fiducial points, the rest of the anatomy can also be registered in the cameras field. Thus the exact positioning of these fiducial points onto the graphic display of the anatomical data from the images can be made. Furthermore, the exact positioning of the probe with its fiducial points 2 and 3 can be thus set quantitatively into the field in a similar way. This corresponds to a series of 3-dimensional coordinate transformations and is a straight-forward mathematical matter. FIG. 2 illustrates another embodiment to the present invention in which more than 2 cameras are involved. Cameras 204 and 205, as well as camera 210, are present and may prealigned or not prealigned prior to surgery. They are anchored on a support structure 230 which holds them rigidly in place and that support, in turn, is clamped by means of clamping means 231 to some stable object relative to the patient's head 206 such as the operating room table or the floor itself. Headholder 232 may be a standard headholder as used in most operations with pin fixation points to the skull illustrated by 233, it too can be anchored to the operating table or to the floor by post 234 and, thus, the optical system above it and the head holder are stabilized relative to each other by means of their attachment to either themselves or to the operating table. Again, the index points 202 and 203 represent the fiducial points for the cameras 204, 205 and 210 and by digitizing the field of these cameras, one can determine the position and orientation of the probe 201. In addition, there are the index points 208A, B, and C which represent independent fiducial points on the patient's head which can be also observed by the camera and the camera can, therefore, check the stability as well as their coordinate reference frame continuously by monitoring these fiducial points on the anatomy itself. There is a typical range of motion of the probe 201 which is practical in such operations and this is illustrated as an example by the dashed cone 240. It must be that the camera can visualize the probe 201 and the fiducial points 202 and 203 everywhere within this working cone. This is typically the range in which the surgeon will be introducing instruments into the cranial opening site illustrated by 207. It is clear that the positions of the cameras 204, 205 and 210 can be prearranged and precalibrated on the bar 230. This may be so that they are pointing isocentrically to the same point in that their visualization fields are precalibrated and preoriented so that everything within the field has a known calibration. This could also be easily checked by taking the platform 230 off at any given time and putting it on a phantom base or some other jig structure which enables instant calibration of the system. It is also true that the head holder 232 may have fiducial lights on it or fiducial points so that it may be referenced relative to the cameras and the entire system becomes an integral digitized calibrated system.

Figure 3:
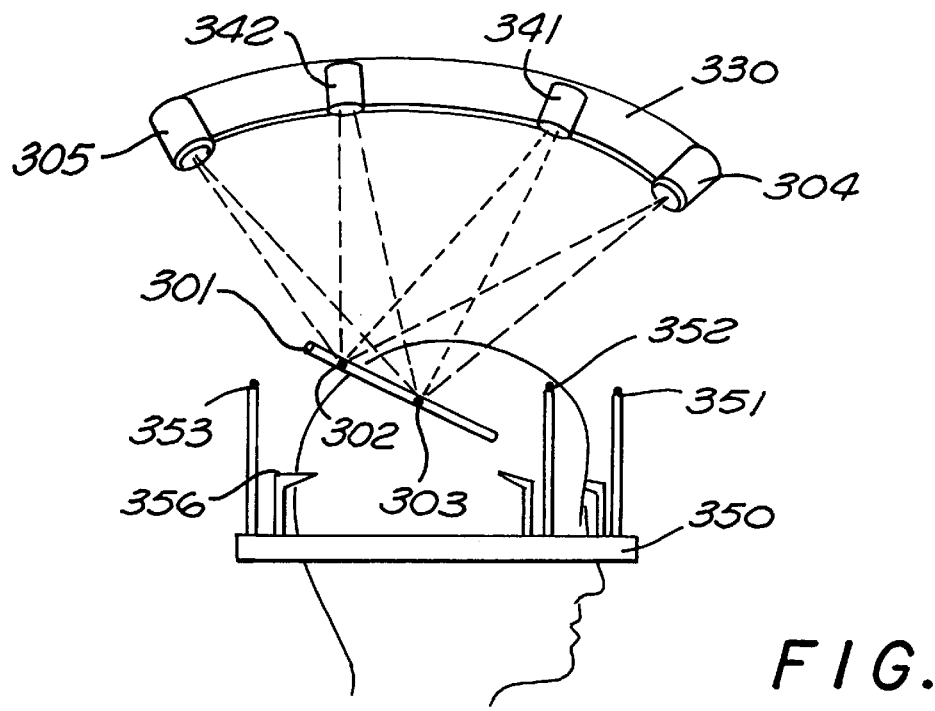
FIG. 3 shows an embodiment of the present invention in which light sources at a distance from the pointer are used to reflect off reflectors on the pointer and the reflected light is detected by video cameras to ascertain the orientation of the space pointer.

FIG. 3 shows another embodiment of the present invention in which external light sources are present as well as the cameras for receiving optical signals. Cameras 304 and 305 are arranged and fixed to bar 330 for positioning. Light sources 342 and 341 are also arranged and attached to the bar 330 so that they aim towards the probe 301 which has reflectors on it, 302 and 303 which reflect the light from the light sources 341 and 342. The cameras detect the reflected light which is illustrated by the dashed light beams shown in FIG. 3. In this way the probe does not have to have any energy source or active light sources, but can be merely a reflector of light. It is also true that the probe itself could be one, long reflective linear arrangement or could have other arrangements of the fiducial points instead of the the linear arrangement 302, which is coaxial with the probe. Any kind of pattern recognition of this type could be detected by the cameras and the corresponding digitization of the probe position and orientation could be made. In this example of FIG. 3 we also show headring 350 which is affixed to the patient's head by a series of head posts 356 anchored securely to the skull. On the headring are fiducial elements 351, 352 and 353 which serve as index points and reference points that can also be detected optically by the cameras 304 and 305. In this way, the ring 350 represents a platform and corresponding coordinate system basis, the position of the coordinate system being referenced by the fiducial points 351, 352 and 353 and monitored in terms of its relative position to the bar 330 and its associated cameras. In this way the entire operative setting could be monitored for any differences in position and position differences can be corrected for if they are determined by the computer graphics associated with the cameras 304 and 305. It is notable that the need for discreet index points such as 302 and 303 on the space pointer is not absolutely necessary. Pattern recognition algorithms in a computer from data from cameras 304 and 305 may simply recognize the shape of the space pointer 301. Thus, the quantitation of its position in the field need not be done by discreet index points on the instrument.

The major advantage of the probe illustrated in FIGS. 1, 2 and 3 are that they are mechanically decoupled from the observing cameras and thus there are no encumbrances of mechanical linkages such as a robotic arm as has been proposed in the past. It is also true that these probes can be made relatively simply and disposable so that the surgeon can throw the probe away after the procedure without incurring great expense.

Figure 4:
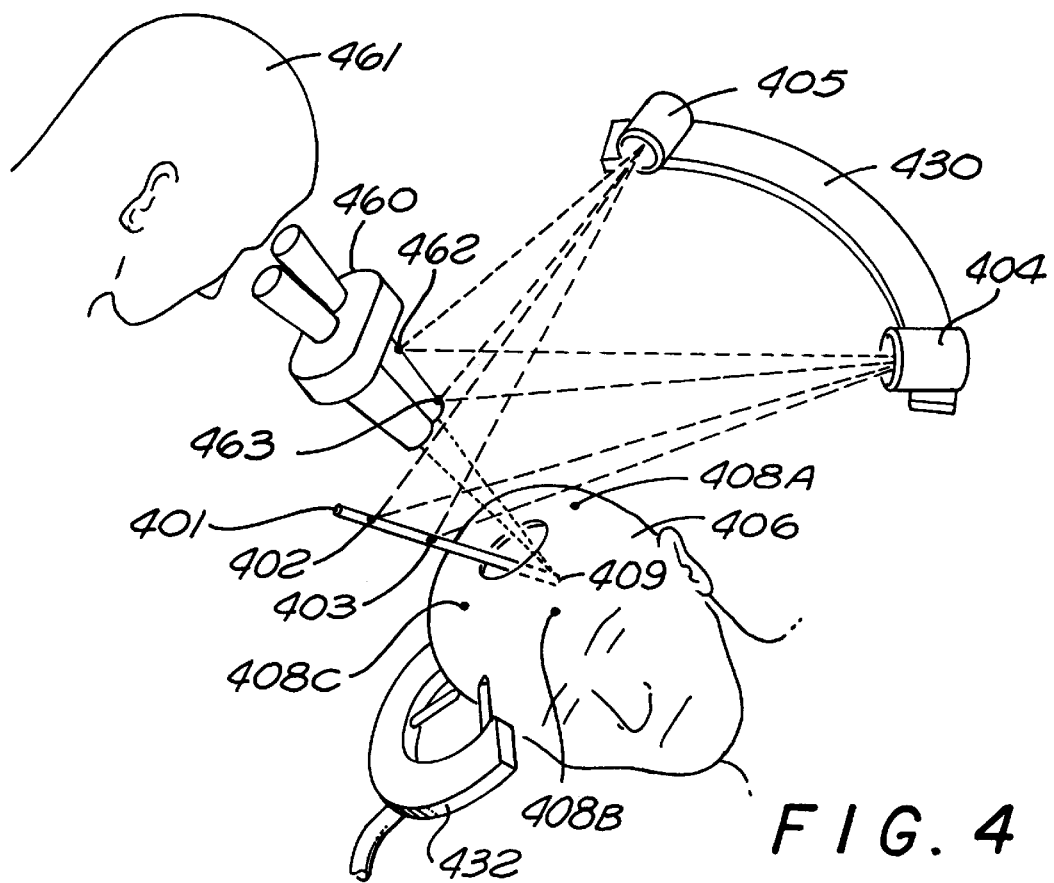
FIG. 4 shows an embodiment of the present invention in which two cameras are used and they visualize the anatomical field together with a space pointer, index marks on the patient's anatomy and a microscope so as to relate the position and aim of the microscope to the anatomy and the space pointer.

FIG. 4 show another embodiment to the present invention with optical digitizing viewing means which involves not only a probe 401, but also an operating microscope 460. The objective here is to determine quantitatively the relationship between the patient's head 406 and its anatomy within it, the space probe 401 and the operating microscope 460. The principle is essentially the same. The patient's head is 406 stabilized by the headholder 432. The microscope has index means 462 and 463 which may be LED point light sources. Similarly, the probe 401 has its index points 402 and 403. Cameras 404 and 405 are affixed to base platform 430 and view the entire field, microscope plus probe plus patient's head. Optical index points 408A, 408B, and 408C may be attached to the patient's scalp or to the headholder to provide referencing to the anatomy of both the probe and the microscope. By this sort of viewing, the relationship of the position of the microscope 460 and its orientation relative to the anatomy can be determined. Thus, one can display on the graphics means the field of view in which the microscope is viewing relative to that anatomy. In this way when computer graphics representations of the anatomy have been made, then computer graphics of the field view with a microscope can also be represented on the graphics display means and, thus, the relationship between what the surgeon 461 is seeing and the computer reconstructed field may be made. This is very important in planning as well as interactive surgical recessions. At the same time, probe 401 may be inserted into the field and the position 409 of its tip can be represented within the actual microscopic viewing field of the microscope 460. The entire surgical array of instruments may be represented graphically so that interactive correction and management of the operation can be made by the computer systems. One can also put other instruments within the field such as scalpels, probes and other devices which the surgeon commonly uses, these being indexed by fiducial marks or simply visualized directly by the cameras and representations of them put onto the graphics display means.

Thus by the index points that we have alluded to in FIGS. 1 through 4 and the associated embodiments, one can relate the various structures including anatomy, probes, microscopes and other instruments together in one graphics display. It should also be said that once this relationship has been established, then the cameras which see the actual objects themselves can make direct overlays of the objects as seen with the graphic representation of these objects as calculated from the imaging prior to surgery. Thus, direct correspondents of shapes and objects can be instantly ascertained by the operator by merely overlaying the graphics display and the actual display together on the same graphics screen.

There are many variations of the embodiments shown in FIGS. 1 through 4. One does not need to have, for example, two video cameras or two or more video cameras pointing in the same plane. They could be non-coplaner and there could be an array of them to encompass a much larger field of space. Such a multi-camera display could be precalibrated or not precalibrated. The cameras could be monitored and stabilized by fixed fiducial points somewhere in the field so that the entire registration and synchronization of all cameras would be possible. The mounting on which the cameras are held could be movable and changed interoperatively to be optimize the position of the cameras while maintaining registration with the subject field. The orientation of the cameras relative to the anatomy, microscope or probe could also be done without the need for fiducial lights such as two and three in FIG. 1 or index fiducial points 8A, 8B, and 8C in FIG. 1. Overall correspondence of the shape of the subject as viewed by the camera could be overlaid and optimized in its matching to the graphics representation of the anatomy taken from the images. Graphic rotation of the image data could be done so as to register the direction of view of the camera relative to the anatomy. This correspondence would then be done by shapes of subjects in the real field vs. shapes of subjects in the graphics field. Such optimization of the two shapes could be done and the direction of the camera thereby determined relative to the field of view. Once that is done, the orientation of the probe 1 or any other shaped object related to a probe could similarly be registered from the camera's point of view. Pattern recognition algorithms be used to determine the orientation of the probe one therefore relative to the orientation of the other subjects such as the head and its orientation relative to the cameras.

The present invention also includes use of one optical camera. Although the examples above illustrate use of two or more cameras, there is utility in even using just one camera to view the surgical field. It can give you a two-dimensional representation in a projected view of the field. One can use this representation and the graphic representation from the image data to register the two views and, thus, align the graphic display in a "camera view". Thus pointers in the field of the camera can be registered directly on to the graphic display view. For example, a pointer moving on the surface of the skin would be registered relative to the graphic view so that you would know where that point is moving relative to this quantitative data that represents the skin and other anatomical structures below the skin. This would have more limited usefulness, but it could also be important. Thus, the application of mounting a single video camera to view a surgical field and representing that visual field on a graphic field so as to bring the two fields into alignment by manipulation of the graphic field in the computer has utility in the surgical setting.

Figure 5:
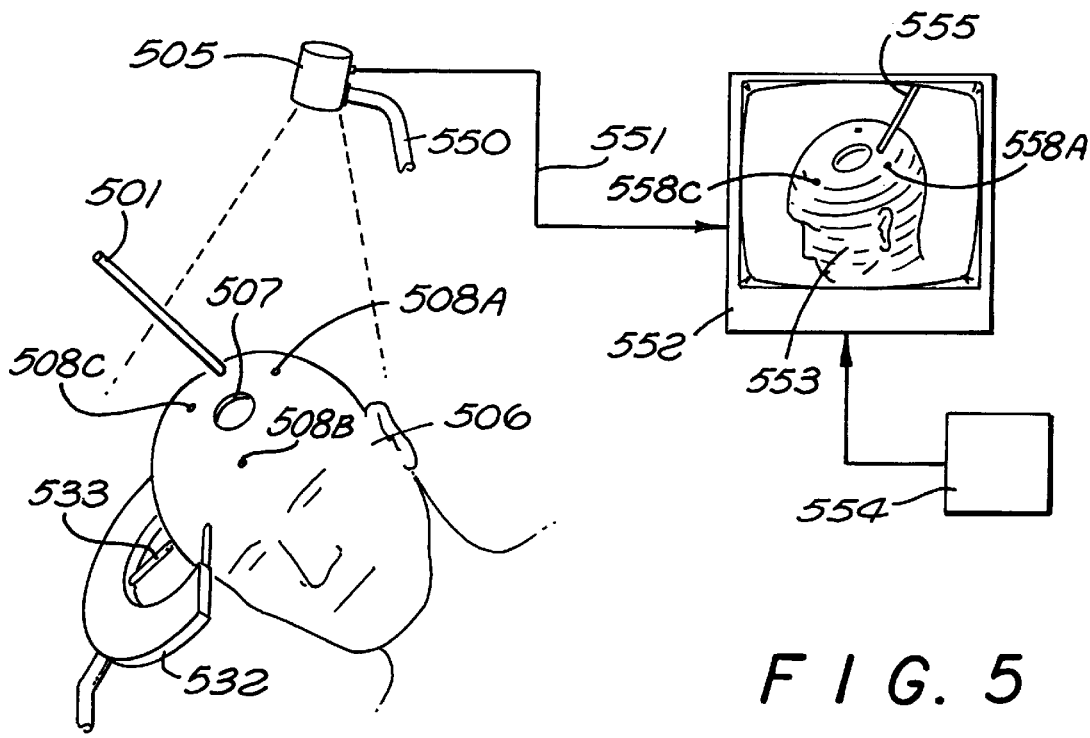
FIG. 5 shows a generalized, signal camera embodiment of the invention where the camera is coupled to a computer graphic means and the view of the camera looking at the patient anatomy is related to image data from image scan means so as to register the camera view and the image data to quantify the camera view field.

FIG. 5 illustrates more specifically the use of one optical viewing camera and registration of its field by computer graphics to image data. In FIG. 5, camera 505 which has been anchored via arm 550 near the surgical field, views the patient's head 506 and objects nearby. The camera is connected via cable 551 to the computer graphics screen 552. The computer graphics screen is cooperatively connected to computer calculation means and storage means and it has represented on its screen image data from the image scanning source 554. This scanning source may be a CT or MRI scanner or it may be a magnetic tape with corresponding data on it. The camera 505 is viewing the head and representation of the head shows on the screen together with image data indicated by the contours 553. In the field, is probe 501 which is seen as 555 on the screen. Also there is a surgical opening 507 and for completeness, the index marks 508A, 508B, and 508C which may aid in orienting what is seen by camera 505 to the graphics image data seen on screen 552. The headholder 532 and associated pins 533 hold firmly the head 506 relative to the camera 505. As shown in the screen 552, the corresponding index points 558A, 558B, and 558C are shown on the screen as well as the actual image of the anatomy and the space probe represented by image 553. Thus, if computer graphics representations of the same anatomy are simultaneously put on the screen, for example, in a different color, then those image data can be scaled, translated, and rotated such that they register with what is seen by the field of view of camera 505. By so doing that, one has in perspective view a registration of the camera data with the image data. Thus when one looks at the image 555, on the computer graphic screen 552 of the actual probe 501, one can see immediately the correspondence of that probe relative to the quantitative stereotactic image data anatomy. Thus in perspective view, one is relating the position of the probe to that stereotactic image data anatomy, and this can be a very useful adjunct to surgery. For example, if one wished to know where to make the surgical opening 507, one could move the probe 501 in actual space relative to the anatomy until one sees the probe in perspective view with its tip over the desired point relative to the image data anatomy seen on screen 552. That would instantly tell you that this is the place to make the surgical bone opening for example. There are many other illustrations of the use and power of this one-camera approach.

Figure 6:
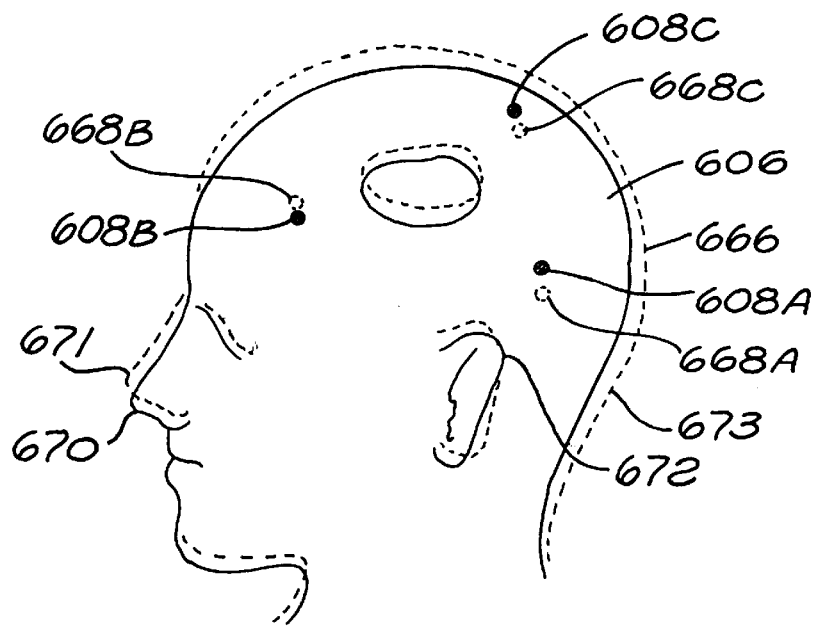
FIG. 6 shows a schematic representation of how camera field data would be registered in position and orientation to analagous image scan data on the same computer graphic display.

FIG. 6 shows how one might register camera anatomical data to image machine-acquired anatomical data as described in the paragraph related to FIG. 5. For example, in FIG. 6 the outline 606 represents the actual contour of the patient's head as seen by the camera 505 in FIG. 5. Also, the point 608A and 608B and 608C are shown as dots and these two are seen by the camera. Furthermore, anatomical landmarks such as 672, the tip of the ear, and 670, the tip of the nose, may be seen by the camera 505 in FIG. 5. The dashed contour in FIG. 6 shows a similar contour reconstructed in a perspective view from, for example, CT slice image data. Such image data can be stacked, can be surface rendered, and can be viewed and oriented from any different direction by computer graphics manipulation. Thus, it is possible to take such "dashed" image data representations, scale them proportionately, rotate them in space, and translate them, such that when you view the dashed and undashed contours on the computer graphics console, the operator can easily trim in the image data or the dashed line 666 such that it matches exactly the solid line 606 on the computer graphics screen. In a similar way, one can make computer graphic manipulations to register the correspondence of the image points from the camera 608A, 608B, and 608C with the corresponding index points 668A, 668B, and 668C, which are illustrated by dashed points in FIG. 6. Registering these two sets of the same physical points in the computer graphics would be an attractable way of registering the entire two perspective views. Similarly, anatomical landmarks which are identifiable such as the computer graphic representation of the tip of the ear 673 and the tip of the nose 671 can be represented and corresponded to the analagous point 672 and 670 from the camera data. The use of different colors, color washes, color transparencies, and other powerful graphic standards as well as mathematical algorithms to optimize the correspondence of these two perspective views are easily put into play at this point to do the job.

Figure 7:
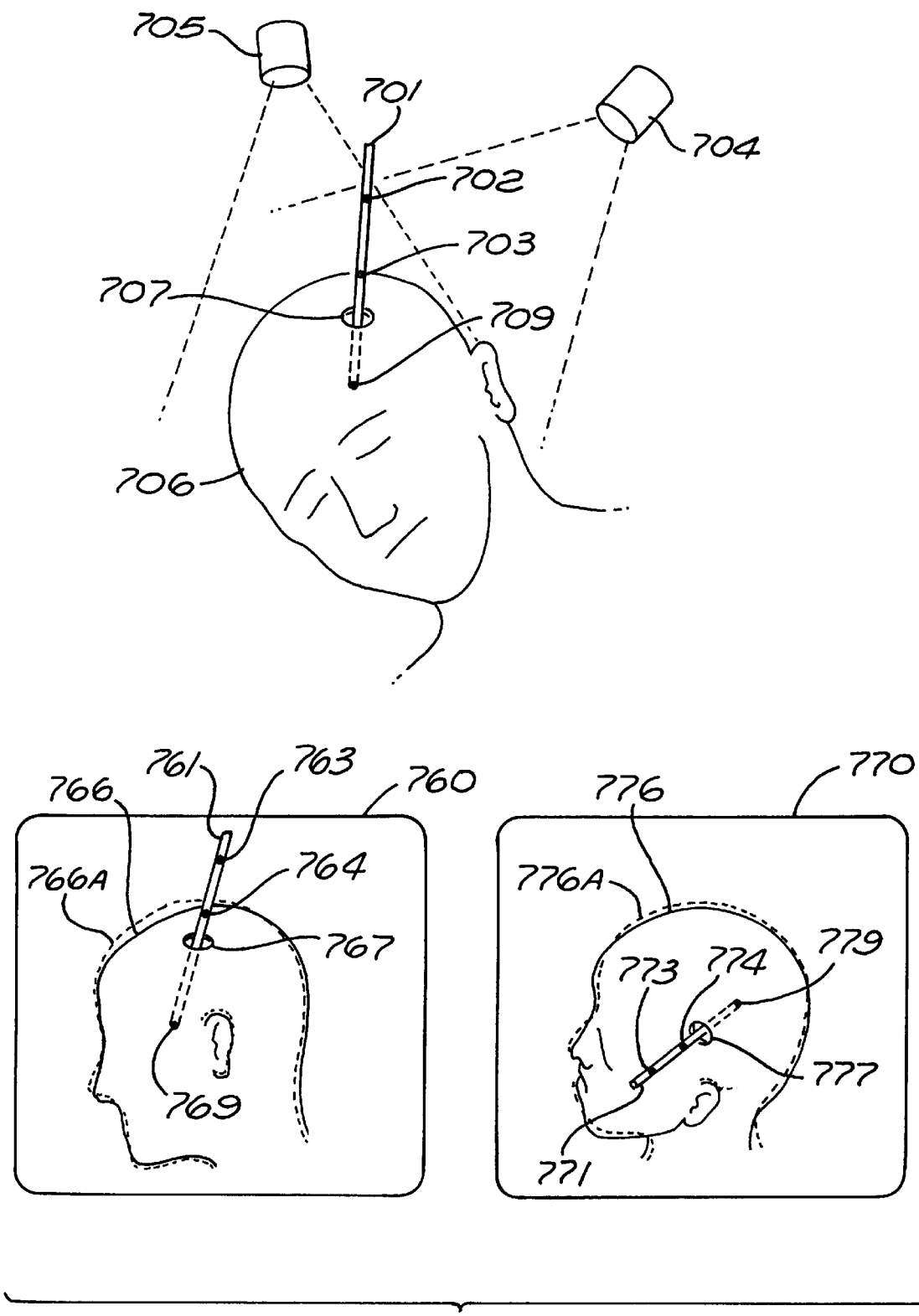
FIG. 7 shows a schematic view of two cameras looking at the anatomical subject with corresponding computer graphic views both of the camera, readout and field-of-view and of the computer graphic representation of the same view.

FIG. 7 illustrates another embodiment of how more than one camera can be used for computer graphic registration and corresponding quantification of an optical view. In the upper portion, one sees two cameras 704 and 705, pointing at arbitrary non-identical directions towards the subject 706. The fields of view are shown with the dashed lines. There is a cranial hole 707 with a probe 701 in it into the depth of the brain with the tip 709 inside the head. Index points 702 and 703 on the probe may or may not be present and are analogous to those discussed in FIG. 1. Each of the cameras will have views as illustrated in the lower portion of FIG. 7 and are displayed on the computer graphic display means 760 and 770. 760 represents, for example, the view of camera 704 and one sees the solid line 766 which is the optical outline as seen by camera 704 of the patient's head. Similarly, the probe 761 is seen through the burr hole 767. By computer graphic translation, rotation and scaling, one can adjust the computer graphic view so that it matches the anatomical view, i.e. the computer graphic perimeter 766A indicated as dash line exactly matches 766. In this way, one knows that one has reproduced graphically with the dashed curve the projected view as seen by 704. Analogously, camera 705 will have its view as seen in graphic display 770 of the outline of the head 776 being matched to the graphic outline of the head 776A. Obviously, index marks, grids or lines on the patient's scalp might help in this registration of the two camera views. Once these views, however, have been registered, uniquely identifiable points in both views can give information on the exact 3-dimensional coordinates of those identifiable points relative to the anatomy as seen from the image data. For example, the points 763 and 773 are identical and correspond to the physical point 702 on the probe. On each of the views 760 and 770 this point represents a projected line as seen from the respective camera. The two lines from the two cameras intersect at a unique point and this can easily be determined as a unique 3-dimensional point referenced to the data from the image scanner as stored in the computer. Thus, the two points 702 and 703 can be determined quantitatively in space relative to the anatomical data, and thus, the quantitative position of the probe and any point on the probe can be determined relative to the image data. In particular, the end of the probe represented by point 709 which is in the depth of the brain and indicated on the graphics display as 769 and 779 respectively can be determined, i.e the 3-dimensional coordinates of that point relative to the 3-dimensional image anatomy can be determined. Thus, there is no particular need for special index marks as shown in FIG. 1. Mere registration of existing anatomical structures relative to camera view and the image data would be sufficient for a full 3-dimensional representation of any instrument such as the probe in FIG. 7 relative to the anatomy. Using special angles such as 90° or stereoscopic views of the cameras could be convenient for such 3-dimensional registration without prior calibration.

It also should be said that for fixed camera positions, the subject itself might be moved so that his optical representation matches the graphic representation. In most cases, it would seem simpler to do the movement of the subject's image data via software, than moving the anatomical subject relative to the cameras, however, both methods could be used for registration of the respective images.

The use of such camera registration with image data eliminates any need of camera field calibration or the need to know relative camera angles.

It should be stated that this technique and the rest of the discussion above is differentiated from a previous attempt at registration of computer graphics to anatomical viewing. This was done by Patrick Kelly in the 1980's, and is reported in the literature in several places. Kelly's approach was to move a surgical microscope to a direction that was determined by image scan data. He would then take reconstructed structures from the image data and project it on a "heads up" display so that the surgeon looking on the microscope could see a graphic representation of what he should be viewing in the microscope field. The procedure of Kelly's was to first calculate the position from graphics of his microscope in terms of the approach angles of the microscope to the anatomy. Once specifying these approach angles, he could superpose the simulated graphics next to the microscope view. There are important conceptual differences between Kelly's method and the method discussed here in the present invention. First, Kelly does not use information, qualitative or quantitative, in the camera view or microscope view to make the correspondence, registration, or quantification of what is seen in the camera view relative to the graphics data. Secondly, he never uses two cameras to quantify the field of the cameras and relate them to the graphic display. Thirdly, he does not use object-related or fiducial identification points seen in one or more camera views to register the views directly to the image data. Thus, Kelly's approach differs in a fundamental way from what is being claimed in this invention.

The present invention includes in its scope the use of one or more cameras in the the context illustrated by FIGS. 1 through 7. It includes the use of a camera together with a computer and computer graphic means to register and relate optical viewing to image data from other scanning and imaging devices. It also relates to the use of such optical and image data correspondences to register and quantify the position of surgical tools such as the space probe or the microscope illustrated in the above examples. It is related to making the associated mathematical transformation from a coordinate system or perspective view seen by one or more cameras to a stereotactic coordinate system related to image data or a corresponding reconstructive perspective view of image data and associated coordinate information from such image data. It relates to the correspondence between objects both anatomical or surgical in a camera view to objects either anatomical or of an index or marker nature as represented from scanner data or extrapolated from scanner data in a computer or computer graphic system. This was given as a specific example from FIG. 1 in the relationship of a mechanical space pointer to index marks and these, in turn, to corresponding quantitative positions in space where index marks has known from image data. Registration of the camera viewing data to the image data may or may not involve index marks, index lines or index localizer devices. It may be done as illustrated in FIGS. 6 and 7 by visual or computer theoretic optimization of registration of camera and image data or camera and reconstructed image data or enhanced camera or manipulated image data. The invention further generalizes the concept of "a camera" to other camera-like devices. These might include an x-ray camera or an x-ray source is point-like and projects through the anatomy to give the image on a detection plane at the opposite side of the anatomy. This data could be projectively reconstructed as though it were reflected light from a single camera as illustrated in the examples above. Thus, the invention subsumes the field of generalized camera viewing or projected image acquisition relative to CT, MRI or angiography acquisition from other imaging means and the registration thereafter to make correspondence between these two image acquisition modalities.

Using more than one camera enables the determination of three-dimensional coordinates and depth of perception. The examples on FIGS. 1 through 4 illustrate this by use of a probe with two fiducial points on it that can be seen and digitized by the two camera views. This invention relates to the use of a video camera to quantitatively relate to graphic display data taken from other imaging means. The correspondence of the data are illustrated by the embodiments above and the discussion above, but those skilled in the art could think of other implementations of the same invention concept. For example, the use of two fiducial points on the probe can be extended to other types of optical fiducial means such as lines, other arrays of points, other geometric patterns and figures that can be recognized easily by computer graphics, artificial intelligence, etc. The two points illustrated in the figures be replaced by a line of light or a line of light and one or more discrete points to encode the direction of the object. The object itself could be recognized by the computer graphics as a line merely by having it of a reflective material or a particular color. The space pointer, for instance, could be white or green and thus show up differently on the TV cameras and in the video display so as to recognize it as the pointer.

Having described herewith the general illustrations of the invention, what I wish to patent by U.S. Letters Patent are the following claims:

1. Apparatus for relating a representation of a patient anatomy generated from a plurality of scanner image data to at least one camera's field-of-image registration of said patient anatomy, said apparatus including:

at least one camera for registering an image of said patient anatomy and at least one one surgical instrument located in relation to said patient anatomy, said camera providing an electronic readout of said at least one camera's field-of-image registration including location of said at least one surgical instrument in relation to said patient anatomy; and, a computer with a graphics display for receiving, processing and displaying said scanner image data and said electronic readout of said at least one camera's field-of-image registration, said computer having software for registering and establishing a correspondence between said at least one camera's field-of-image registration and said scanner image data based on information related to index points that are determinable in both said at least one camera's field-of-image registration and said scanner image data, whereby said information relating to said at least one surgical instrument in said at least one camera's field-of-image registration can be directly related to said patient anatomy; and fiducial markers for connection to said patient anatomy and determinable in both the scanner image data and the at least one camera's field-of-image registration to facilitate registering the at least one camera's field-of-image registration and the scanner image data on the graphics display of said computer.

2. Apparatus for relating a representation of a patient anatomy generated from a plurality of scanner image data to at least one camera's field-of-image registration of said patient anatomy, said apparatus including:
  at least one camera for registering an image of said patient anatomy and at least one surgical instrument located in relation to said patient anatomy, said camera providing an electronic readout of said at least one camera's field-of-image registration including location of said at least one surgical instrument in relation to said patient anatomy; and,
  a computer with a graphics display for receiving, processing and displaying said scanner image data and said electronic readout of said at least one camera's field-of-image registration, said computer having software for registering and establishing a correspondence between said at least one camera's field-of-image registration and said scanner image data based on information related to index points that are determinable in both said at least one camera's field-of-image registration and said scanner image data, whereby said information relating to said surgical instruments in said at least one camera's field-of-image registration can be directly related to said patient anatomy; and
  said computer includes hardware and related software to rotate, translate, and scale said scanner image data to match said camera's field-of-image registration as displayed on the graphics display of said computer.

3. Apparatus for relating a representation of a patient anatomy generated from a plurality of scanner image data to at least one camera's field-of-image registration of said patient anatomy including:
  at least one camera for registering images of said patient anatomy and at least one surgical instrument located in relation to said patient anatomy, said at least one camera providing an electronic readout of said at least one camera's field-of-image registration;
  a computer with a graphic display for displaying said scanner image data and said electronic readout, said computer having software for registering said electronic readout of said at least one camera and said scanner image data so that both said at least one camera's field-of-image registration and said scanner image data are visually displayed on said graphic display facilitating said at least one camera's field-of-image registration to be directly related to said scanner image data and said at least one surgical instruments in said at least one camera's field-of-image registration to be visually and quantitatively related to said patient anatomy either both on the surface of the patient anatomy or in depth in the patient anatomy as seen from said scanner image data on said graphic display; and
  fiducial markers for placement on said patient anatomy and determinable in both the scanner image data and said at least one camera's field-of-image registration to facilitate said registration of said at least one camera's field-of-image registration and said scanner image data on said graphic display.

4. Apparatus for quantitative registration of a patient anatomy with a computer graphic representation generated from a plurality of image data of said patient anatomy taken from an imaging machine and for registration of said image data to a surgical apparatus located near said patient anatomy, including:
  at least one optical camera with quantitative electronic readout of a field-of-image registration thereof, said at least one optical camera being positioned with respect to said patient anatomy to provide said field-of-image registration including said patient anatomy;
  a computer graphics display for displaying said image data of said patient anatomy and said electronic readout of said at least one optical camera's field-of-image registration of said patient anatomy; and,
  a registration device coupled with said at least one optical camera for aligning said image data and said electronic readout of said at least one optical camera and for providing a visual representation thereof on said computer graphics display means whereby an operator can visually and quantitatively observe the spatial relationship of said field-of-image registration of said at least one optical camera to said image data of said patient anatomy and simultaneously the spatial relationship of said surgical apparatus to said patient anatomy; and
  detachable markers for placement on said patient anatomy that are determinable in both said image data and said electronic readout of said field-of-image registration of said at least one optical camera so that when said markers as determined both in said image data and said electronic readout are brought into quantitative correspondence in said computer graphics display, registration of the image data with said electronic readout occurs.

5. A method for determining quantitatively the position of a surgical apparatus relative to a patient's anatomy in a surgical setting, said method comprising the steps of:
  positioning at least one optical camera with electronic readout means relative to said patient's anatomy, said at least one optical camera providing a field-of-image registration of said patient's anatomy and said surgical apparatus;
  placing detectable instrument markers at known positions on said surgical apparatus which are determinable by said at least one optical camera;
  attaching body markers to said patient anatomy which can be determined by said at least one optical camera, said body markers having a known relationship to said patient anatomy from image data taken from at least one imaging device;
  registering images of said patient anatomy, said instrument markers, and said body markers with said at least one optical camera, and using a computer to register the image data with said electronic readout data from said field-of-image registration of said at least one optical camera by registering the positions of said body markers in said image data and said electronic readout data; and
  determining the position of said instrument markers and thus said surgical apparatus relative to said patient anatomy by using said computer and by using the relation of said body markers and said instrument markers as determined from said electronic readout of said field-of-image registration.

6. Apparatus for relating a representation of a patient anatomy generated from a plurality of scanner image data to at least one camera's field-of-image registration of said patient anatomy, including:
  at least one camera for registering images of said patient anatomy and at least one surgical instrument used for said patient anatomy, said camera having an electronic readout of said at least one camera's field-of-image registration;
  fiducial markers for placement on said patient anatomy and determinable in both the scanner image data and said at least one camera's field-of-image registration;
  a computer with a graphics display for receiving, processing and displaying said scanner image data and said camera electronic readout, with both said scanner image data and said camera electronic readout being displayed in proximity to each other, said computer having software for registering and establishing a correspondence between said at least one camera's field-of-image registration and said scanner image data based on information related to the fiducial markers determinable in both said at least one camera's field-of-image registration and said scanner image data, whereby information on said at least one camera's field-of-image registration can be directly related to said scanner image data, and said at least one surgical instrument in said at least one camera's field-of-image registration can be directly related to said patient anatomy.

7. Apparatus for relating a representation of a patient's anatomy generated from a plurality of scanner image data to at least one camera's field-of-image registration of said patient's anatomy, including:

at least one camera for registering an image of said patient's anatomy and at least one surgical instrument located in relation to said patient's anatomy, said camera providing an electronic readout of said at least one camera's field-of-image registration including location of said at least one surgical instrument in relation to said patient's anatomy; and, a computer with a graphics display for receiving, processing and displaying said scanner image data and said electronic readout of said at least one camera's field-of-image registration, said computer having software for registering and establishing a correspondence between said at least one camera's field-of-image registration and said scanner image data based on information related to index points that are determinable in both said at least one camera's field-of-image registration and said scanner image data, whereby said information relating to said at least one surgical instrument in said at least one camera's field-of-image registration can be directly related to said patient's anatomy, said computer further including hardware and related software to rotate, translate, and scale said scanner image data to match said camera's field-of-image registration as displayed on the graphics display of said computer.

* * * * *